(12) United States Patent
Stouffer

(10) Patent No.: US 10,058,696 B2
(45) Date of Patent: Aug. 28, 2018

(54) COMPOSITE METAL CONTAINER FOR CONTROL MODULE OF ELECTRICAL STIMULATION SYSTEMS AND METHODS OF MAKING AND USING

(71) Applicant: Boston Scientific Neuromodulation Corporation, Valencia, CA (US)

(72) Inventor: Thomas W. Stouffer, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 137 days.

(21) Appl. No.: 15/068,153

(22) Filed: Mar. 11, 2016

(65) Prior Publication Data

US 2016/0271387 A1  Sep. 22, 2016

Related U.S. Application Data

(60) Provisional application No. 62/133,856, filed on Mar. 16, 2015.

(51) Int. Cl.

| A61N 1/00 | (2006.01) |
|---|---|
| A61N 1/05 | (2006.01) |
| A61N 1/375 | (2006.01) |
| A61N 1/378 | (2006.01) |
| A61N 1/36 | (2006.01) |
| A61N 1/37 | (2006.01) |
| A61N 1/372 | (2006.01) |

(52) U.S. Cl.
CPC ........... *A61N 1/05* (2013.01); *A61N 1/36142* (2013.01); *A61N 1/375* (2013.01); *A61N 1/3718* (2013.01); *A61N 1/3752* (2013.01); *A61N 1/3787* (2013.01); *A61N 1/37223* (2013.01)

(58) Field of Classification Search
USPC .................................................... 607/33, 116
See application file for complete search history.

(56) References Cited

U.S. PATENT DOCUMENTS

| 6,181,969 B1 | 1/2001 | Gord |
|---|---|---|
| 6,516,227 B1 | 2/2003 | Meadows et al. |

(Continued)

OTHER PUBLICATIONS

International Search Report and Written Opinion for PCT/US2016/022097 dated Jun. 3, 2016.

*Primary Examiner* — Nicole F Johnson
(74) *Attorney, Agent, or Firm* — Lowe Graham Jones PLLC; Bruce E. Black

(57) ABSTRACT

An implantable control module for an electrical stimulation system includes a connector to couple to a lead or lead extension; an electronics housing coupled to the connector and having a first major surface, a second major surface, and at least one side surface; and an electronic subassembly disposed within the electronics housing. The electronics housing includes a first portion formed of a first conductive material and a second portion formed of a second conductive material. The second portion forms at least part of the first major surface and extends to form an adjacent region of the side surface or the second major surface. In some embodiments, the first conductive material has a resistivity that is no more than 50% of a resistivity of the second conductive material. In some embodiments, the first conductive material is titanium and the second conductive material is a titanium alloy.

20 Claims, 7 Drawing Sheets

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 8/2004 | Meadows et al. |
| 7,174,212 B1 | 2/2007 | Klehn et al. |
| 7,244,150 B1 | 7/2007 | Brase et al. |
| 7,437,193 B2 | 10/2008 | Parramon et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,364,278 B2 | 1/2013 | Pianca et al. |
| 8,862,235 B1 | 10/2014 | Stover et al. |
| 2006/0167534 A1 | 7/2006 | Malinowski |
| 2007/0150036 A1 | 6/2007 | Anderson |
| 2008/0103556 A1* | 5/2008 | Li .................... A61L 31/022 607/61 |
| 2013/0197610 A1* | 8/2013 | Kelsch .............. B21D 26/021 607/72 |
| 2013/0274820 A1 | 10/2013 | Malinowski et al. |
| 2014/0238737 A1 | 8/2014 | Backman |
| 2015/0066113 A1 | 3/2015 | Van Funderburk |

\* cited by examiner

COMPOSITE METAL CONTAINER FOR CONTROL MODULE OF ELECTRICAL STIMULATION SYSTEMS AND METHODS OF MAKING AND USING

CROSS-REFERENCE TO RELATED APPLICATIONS

This application claims the benefit under 35 U.S.C. § 119(e) of U.S. Provisional Patent Application Ser. No. 62/133,856, filed Mar. 16, 2015, which is incorporated herein by reference.

FIELD

The present invention is directed to the area of implantable electrical stimulation systems and methods of making and using the systems. The present invention is also directed to implantable electrical stimulation leads having a control module with a composite metal container, as well as methods of making and using the leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One embodiment is an implantable control module for an electrical stimulation system. The control module includes a connector configured and arranged to couple to a lead or lead extension; an electronics housing coupled to the connector and having a first major surface, a second major surface opposite the first major surface, and at least one side surface coupling the first and second major surfaces; and an electronic subassembly disposed within the electronics housing and configured and arranged to electrically couple to the lead or lead extension through the connector. The electronics housing includes a first portion formed of a first conductive material and a second portion formed of a second conductive material. The first conductive material has a resistivity that is no more than 50% of a resistivity of the second conductive material. The second portion forms at least a region of the first major surface and extends to form an adjacent region of the at least one side surface or the second major surface. In at least some embodiments, the first conductive material is titanium and the second conductive material is a titanium alloy.

Another embodiment is an implantable control module for an electrical stimulation system. The control module includes a connector configured and arranged to couple to a lead or lead extension; an electronics housing coupled to the connector and having a first major surface, a second major surface opposite the first major surface, and at least one side surface coupling the first and second major surfaces; and an electronic subassembly disposed within the electronics housing and configured and arranged to electrically couple to the lead or lead extension through the connector. The electronics housing includes a first portion formed of a first conductive material and a second portion formed of a second conductive material. The first conductive material is titanium and the second conductive material is a titanium alloy. The second portion forms at least a region of the first major surface and extends to form an adjacent region of the at least one side surface or the second major surface.

In at least some embodiments of any of the control modules described above, the first conductive material has a resistivity that is no more than 40% or 33% of a resistivity of the second conductive material.

In at least some embodiments of any of the control modules described above, the second portion extends to form the adjacent region of the at least one side surface and further extends to form an adjacent region of the second major surface. In at least some embodiments of any of the control modules described above, the second portion is contiguous. In at least some embodiments of any of the control modules described above, the second portion extends around an entire circumference of the control module. In at least some embodiments of any of the control modules described above, the first portion is contiguous. In at least some embodiments of any of the control modules described above, the first portion includes a first part and a second part, where the second portion separates the first part from the second part.

In at least some embodiments of any of the control modules described above, the connector defines one or more ports configured and arranged to receive a proximal end of a lead or lead extension. In at least some embodiments, the connector includes a plurality of connector contacts disposed within the connector and configured and arranged for making contact with terminals disposed on the proximal end of the lead or lead extension. In at least some embodiments, the control module further includes a feedthrough assembly disposed between the connector housing and the electronics housing and including a plurality of conductive feedthroughs electrically coupling the electronic subassembly to the connector contacts.

Yet another embodiments is an electrical stimulation system including any of the control modules describe above; and a lead coupleable to the control module. The lead includes a proximal end portion, a distal end portion, electrodes disposed along the distal end portion, and terminals disposed along the proximal end portion and electrically coupled to the electrodes. In at least some embodiments, the electrical stimulation system also includes a lead extension coupleable to the lead and the control module.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having a control module with a composite metal container, as well as methods of making and using the leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
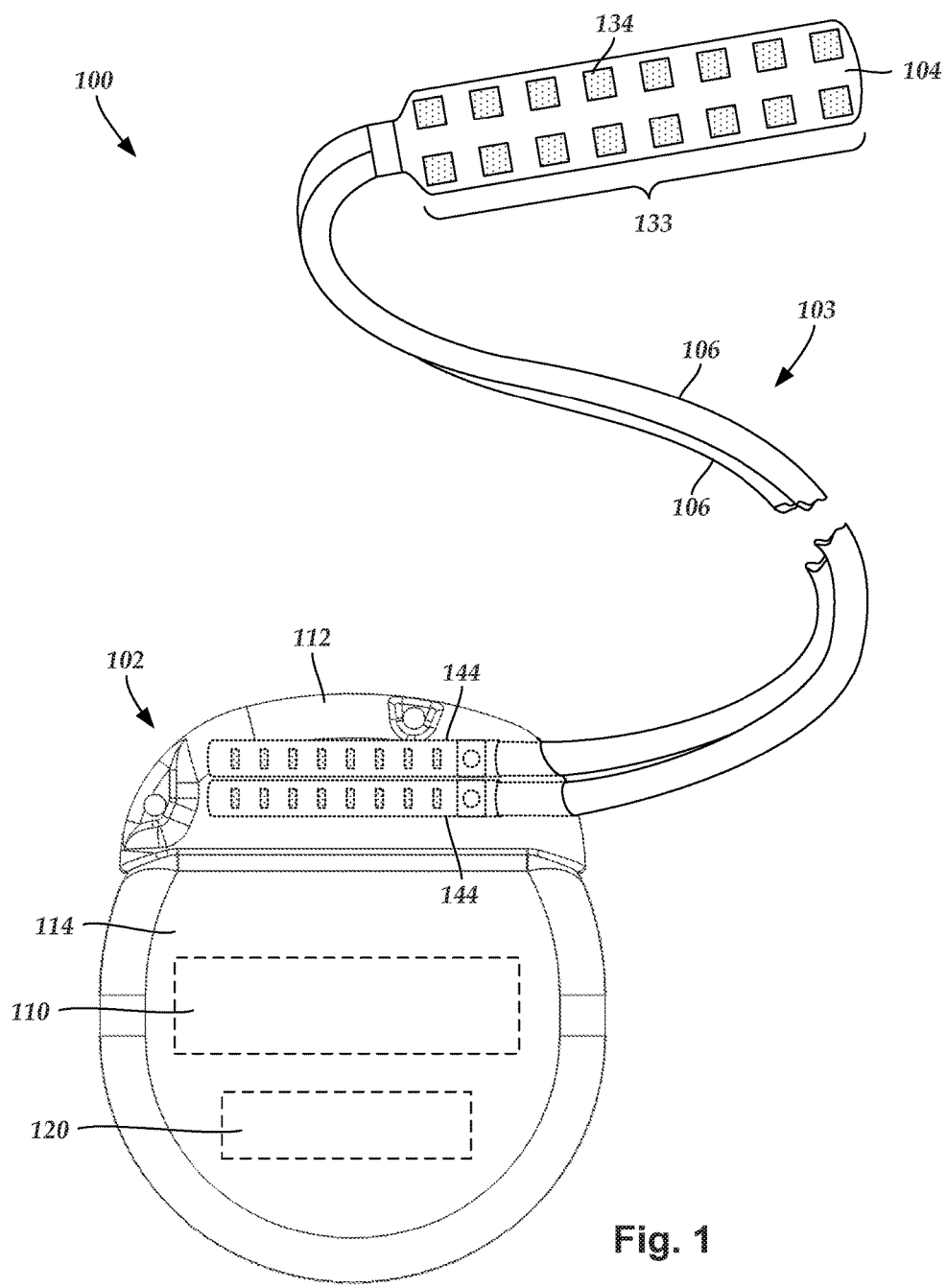
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array 133 of electrodes, such as electrode 134, is disposed on the paddle body 104, and an array of terminals (e.g., 310 in FIG. 3A-3B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
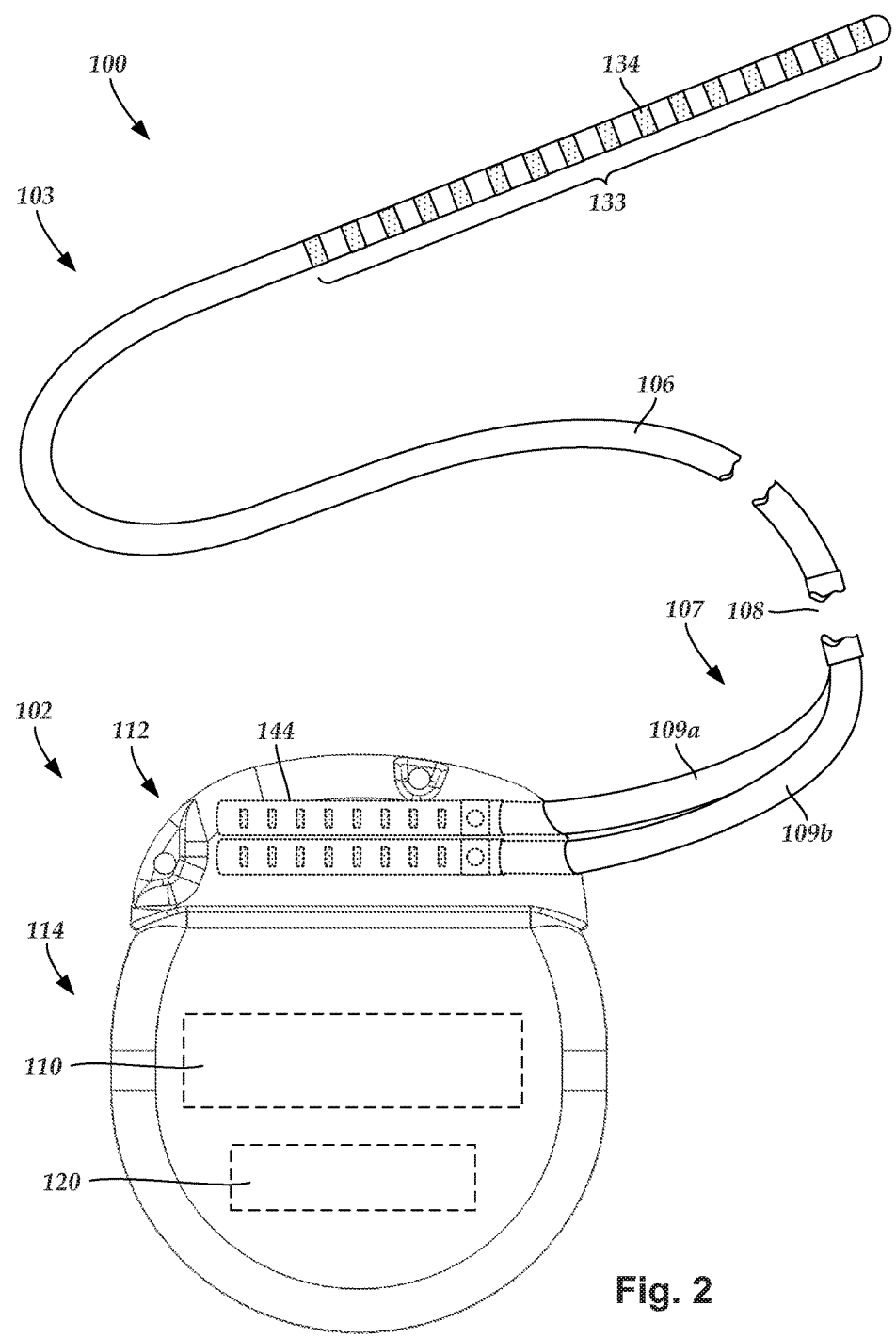
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (324 in FIG. 3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

With reference to FIGS. 1 and 2, the control module 102 typically includes a connector housing 112 and a metal electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
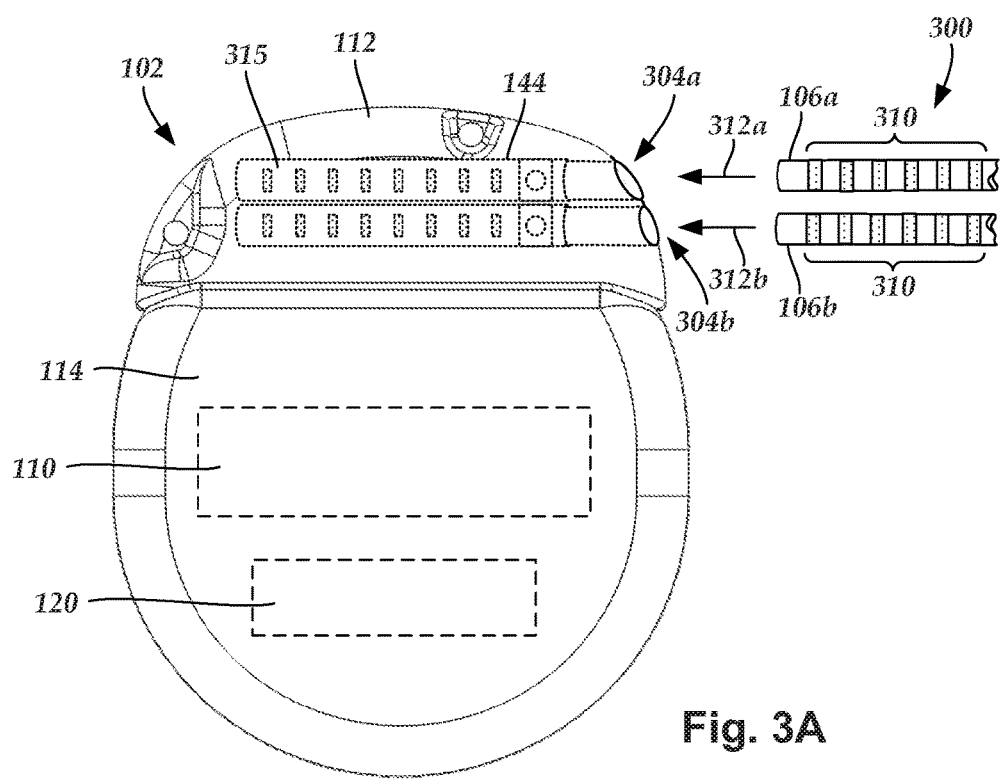
FIG. 3A is a schematic view of one embodiment of the control module of FIG. 1 configured and arranged to electrically couple to an elongated device, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 315 in FIG. 3A). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312*a* and 312*b*. In FIG. 3A (and in other figures), the connector housing 112 is shown having two ports 304*a* and 304*b*. The connector housing 112 can define any suitable number of ports including, for example, one, two, three, four, five, six, seven, eight, or more ports.

The control module connector 144 also includes a plurality of connector contacts, such as connector contact 315, disposed within each port 304*a* and 304*b*. When the elongated device 300 is inserted into the ports 304*a* and 304*b*, the connector contacts 315 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

Figure 3B:
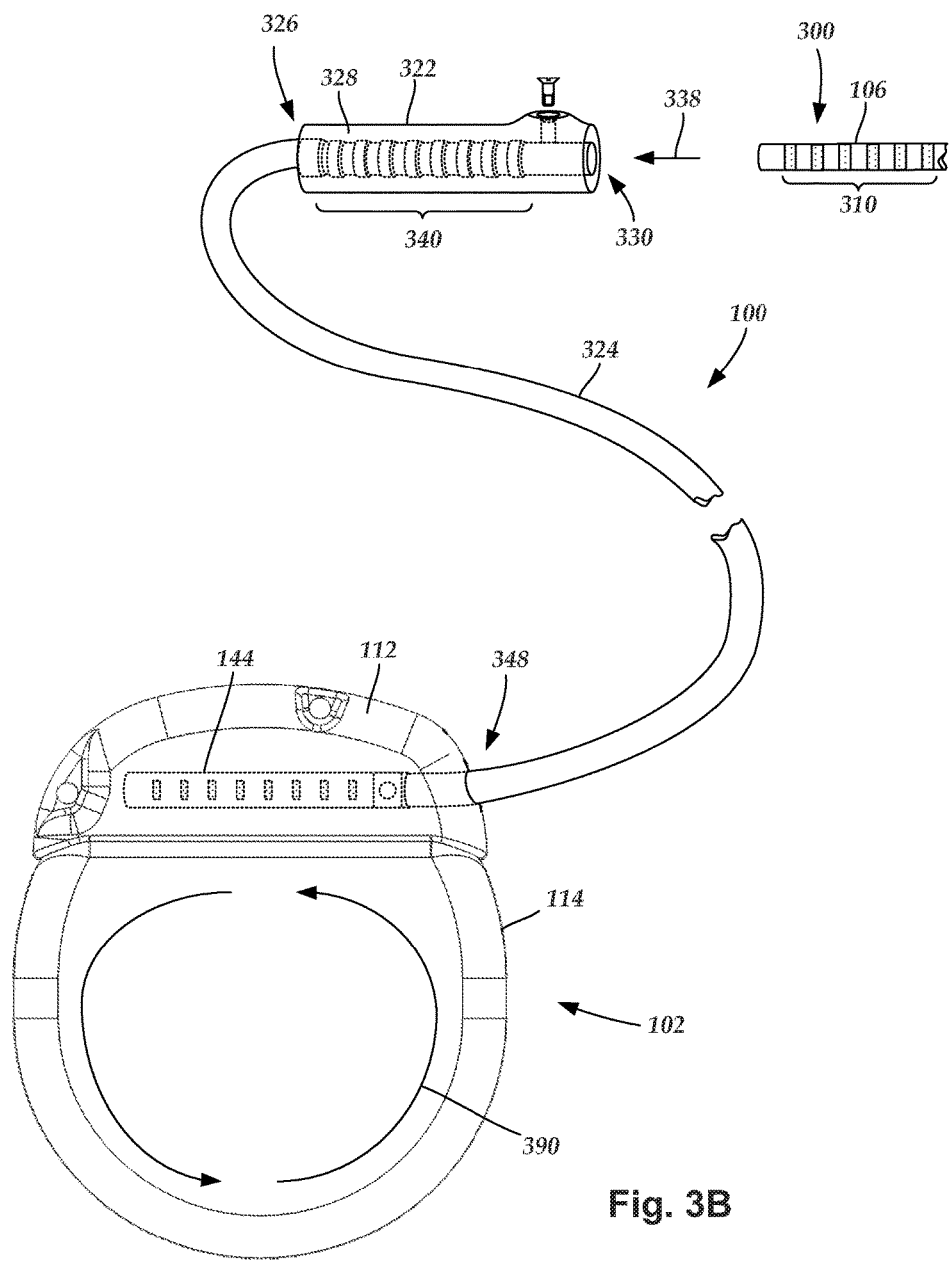
FIG. 3B is a schematic view of one embodiment of a lead extension configured and arranged to electrically couple the elongated device of FIG. 2 to the control module of FIG. 1, according to the invention.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 107 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contacts 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Figure 4:
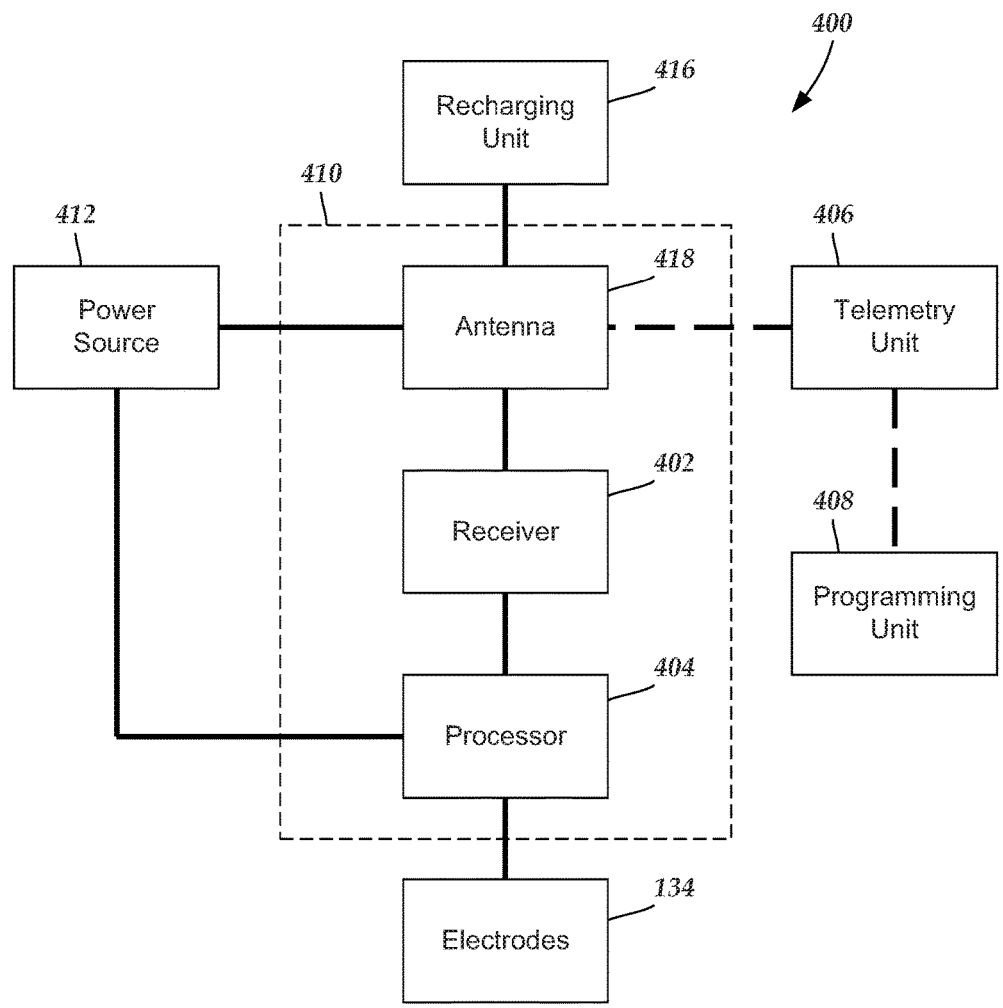
FIG. 4 is a schematic overview of one embodiment of components of a stimulation system, including an electronic subassembly disposed within a control module, according to the invention.

FIG. 4 is a schematic overview of one embodiment of components of an electrical stimulation system 400 including an electronic subassembly 410 disposed within a control module. It will be understood that the electrical stimulation system can include more, fewer, or different components and can have a variety of different configurations including those configurations disclosed in the stimulator references cited herein.

Some of the components (for example, a power source 412, an antenna 418, a receiver 402, and a processor 404) of the electrical stimulation system can be positioned on one or more circuit boards or similar carriers within a sealed housing of an implantable pulse generator, if desired. Any power source 412 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 4,437,193, incorporated herein by reference.

As another alternative, power can be supplied by an external power source through inductive coupling via the optional antenna 418 or a secondary antenna. The external power source can be in a device that is mounted on the skin of the user or in a unit that is provided near the user on a permanent or periodic basis.

If the power source 412 is a rechargeable battery, the battery may be recharged using the optional antenna 418, if desired. Power can be provided to the battery for recharging by inductively coupling the battery through the antenna to a recharging unit 416 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 404 is generally included to control the timing and electrical characteristics of the electrical stimulation system. For example, the processor 404 can, if desired, control one or more of the timing, frequency, strength, duration, and waveform of the pulses. In addition, the processor 404 can select which electrodes can be used to provide stimulation, if desired. In some embodiments, the processor 404 selects which electrode(s) are cathodes and which electrode(s) are anodes. In some embodiments, the processor 404 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 408 that, for example, allows modification of pulse characteristics. In the illustrated embodiment, the processor 404 is coupled to a receiver 402 which, in turn, is coupled to the optional antenna 418. This allows the processor 404 to receive instructions from an external source to, for example, direct the pulse characteristics and the selection of electrodes, if desired.

In one embodiment, the antenna 418 is capable of receiving signals (e.g., RF signals) from an external telemetry unit 406 which is programmed by the programming unit 408. The programming unit 408 can be external to, or part of, the telemetry unit 406. The telemetry unit 406 can be a device that is worn on the skin of the user or can be carried by the user and can have a form similar to a pager, cellular phone, or remote control, if desired. As another alternative, the telemetry unit 406 may not be worn or carried by the user but may only be available at a home station or at a clinician's office. The programming unit 408 can be any unit that can provide information to the telemetry unit 406 for transmission to the electrical stimulation system 400. The programming unit 408 can be part of the telemetry unit 406 or can provide signals or information to the telemetry unit 406 via a wireless or wired connection. One example of a suitable programming unit is a computer operated by the user or clinician to send signals to the telemetry unit 406.

The signals sent to the processor 404 via the antenna 418 and the receiver 402 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 400 to cease operation, to start operation, to start charging the battery, or to stop charging the battery. In other embodiments, the stimulation system does not include the antenna 418 or receiver 402 and the processor 404 operates as programmed.

Optionally, the electrical stimulation system 400 may include a transmitter (not shown) coupled to the processor 404 and the antenna 418 for transmitting signals back to the telemetry unit 406 or another unit capable of receiving the signals. For example, the electrical stimulation system 400 may transmit signals indicating whether the electrical stimulation system 400 is operating properly or not or indicating when the battery needs to be charged or the level of charge remaining in the battery. The processor 404 may also be capable of transmitting information about the pulse characteristics so that a user or clinician can determine or verify the characteristics.

The electronics housing 114 of the control module 102 can be formed using metals (including alloys). Some metals can be readily drawn or molded into the desired shape for the electronics housing. One example is Grade 1 titanium (also referred to as CP (commercially pure) Grade 1 Titanium; see, for example, ASME SB-265, incorporated herein by reference.) The term "titanium", as contrasted with "titanium alloy", as used herein, unless indicated otherwise, means commercially pure titanium including, but not necessarily limited to, Grade 1 to Grade 4 titanium.

Unfortunately, materials, such as Grade 1 titanium, which can be readily drawn or molded into desired shapes also often have a relatively low resistance. As described above, the control module has an antenna 418 (FIG. 4) to receive electromagnetic signals from external sources to provide instructions, inductive charging energy for a battery, or any combination thereof or the like. These external electromagnetic signals, however, can induce current loops 390 (FIG. 3B) in the metal electronics housing, particularly if the metal of the electronics housing has a relatively low resistance. The induced current loops tend to block or reduce the penetration of the external electromagnetic signals into the electronics housing 114 for reception by the antenna 418 of the control module. Such blockage or reduction of the penetration of electrical signals can reduce the efficiency of inductive battery charging, telemetry between the control module and an external telemetry unit or programming unit, or other electrical single communication with the control module.

Other metals, such as Grade 23 titanium alloy (which contains, for example, 6% aluminum, 4% vanadium, 0.13% (maximum) oxygen) or Grade 5 titanium alloy (6% aluminum, 4% vanadium, 0.25% (maximum) iron, 0.2% (maximum) oxygen) or titanium 6/4 (or titanium 6-4 or titanium 6Al4V—for example, 6% aluminum, 4% vanadium), have a larger resistance, but are more difficult to draw or mold. In particular, Grade 23 titanium and Grade 5 titanium (which are alloys of titanium with aluminum and vanadium) have a resistivity that is at least three or four times that of grade 1 titanium. It can be difficult to form an electronics housing using such metals due to the difficulty in forming complex or curved shapes.

An electronics housing can be formed as a composite structure containing one or more sections that are made from a drawable, low resistance material (for example, Grade 1 titanium) and one or more sections that are made from a higher resistance material (for example, Grade 23 titanium) that is not drawn or molded, but is instead formed from one or more flat or bent sheets of metal. The different portions of the composite housing are arranged to reduce or minimize eddy current loops in the electronics housing by placing the higher resistance material on surfaces and edges of the electronics housing. In at least some embodiments, the electronics housing can include the low resistance material to form the curved portions of the housing that are more easily generated by drawing, molding, to the like and the higher resistance material can be provided as flat or bent sheets of metal on the surfaces of the housing to reduce or minimize eddy currents. The portions can be welded or otherwise coupled together to form the electronics housing.

Using the higher resistance material, with the consequent reduction in eddy currents, can result in better penetration of electrical signals into the electronics housing 114 for reception by the antenna 418 of the control module, as compared to an electronics housing formed solely of the lower resistance material. The composite housing can increase the efficiency of inductive battery charging, telemetry between the control module and an external telemetry unit or programming unit, or other electrical single communication with the control module.

Figure 5:
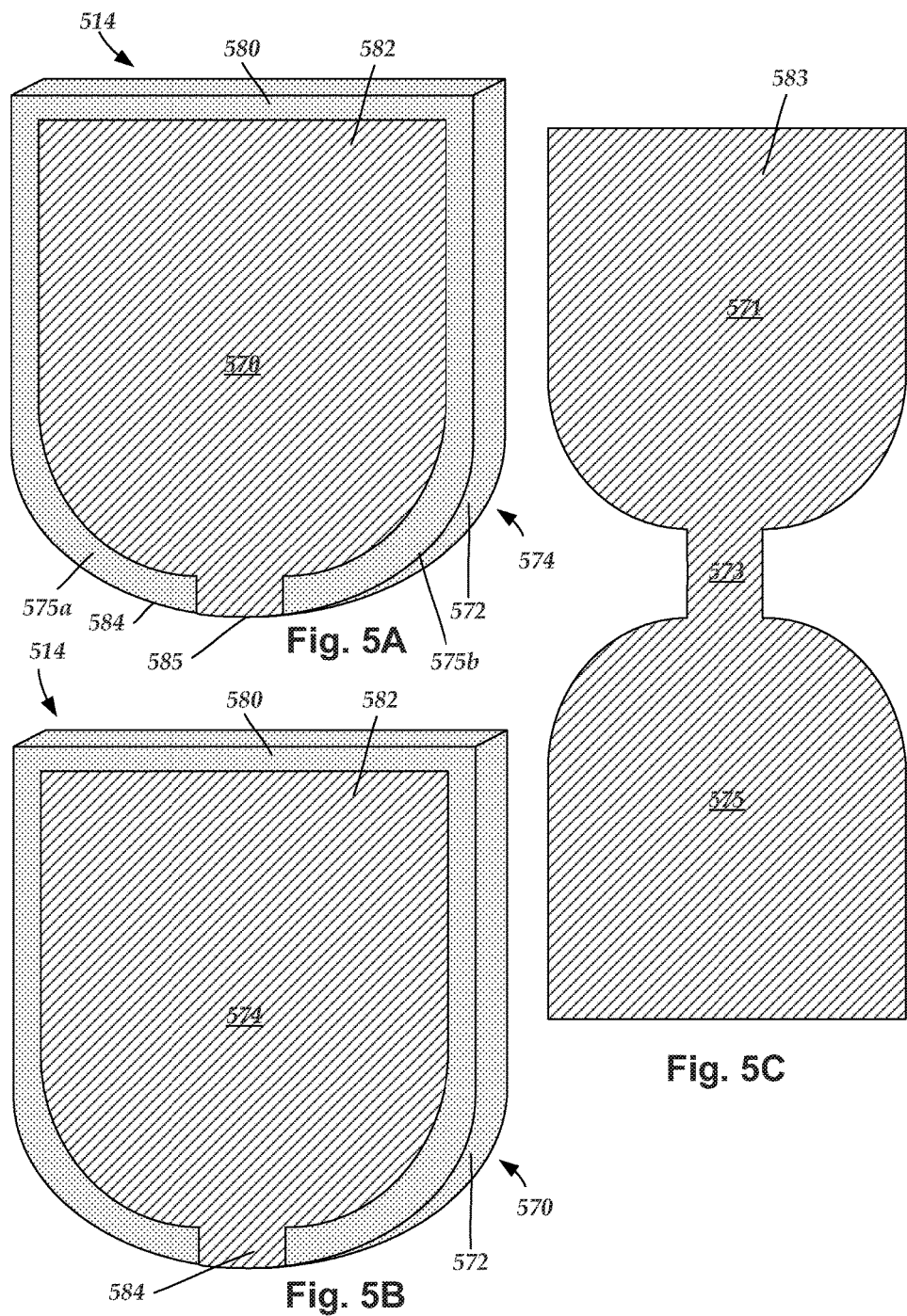
FIG. 5A is a schematic front view of one embodiment of a composite electronics housing of a control module, according to the invention.
FIG. 5B is a schematic back view of the composite electronics housing of FIG. 5A, according to the invention.
FIG. 5C is a schematic view of one embodiment of a portion of the composite electronics housing of FIG. 5A during manufacture, according to the invention.

FIGS. 5A and 5B illustrate the front and back of one embodiment of an electronics housing 514 of a control module (see, control module 102 of FIGS. 1-3B) having a first major surface 570, a second major surface 574 opposite the first major surface, and at least one side surface 572 coupling the first and second major surfaces. The metal electronics housing 514 has at least two portions; at least one first portion 580 that is formed of a first conductive material and at least one second portion 582 that is formed of a second conductive material different from the first conductive material. It will be understood that the electronics housing can be formed with more than one first portion or more than one second portion or any combination thereof. The portion(s) 580 of first conductive material and the portion(s) 582 of second conductive material are welded or otherwise joined together to form the electronics housing 514.

In at least some embodiments, the first conductive material has a resistivity that is no more than 50%, 40%, 35%, 33%, 30%, or 25% of the resistivity of the second conductive material. In at least some embodiments, the first conductive material is titanium (for example, Grade 1 titanium) and the second conductive material is a titanium alloy (for example, Grade 5 or Grade 23 titanium).

The first portion 580 may include one or more curved surfaces (for example, surfaces 575a, 575b) which may be formed by drawing or otherwise shaping the first conductive material. The second portion 582 is preferably configured so that it can be formed from one or more flat sheets of material that can be bent into the second portion. FIG. 5C illustrates one example of a flat sheet 583 of material that can be bent to form the second portion 582 of FIGS. 5A and 5B. This flat sheet 583 includes a region 571 that forms part of the first major surface 570 of the electronics housing, a region 573 that forms part of the side surface 572 of the electronics housing, and a region 575 that forms part of the first major surface 574 of the electronics housing. The metal sheet 583 can be cut into the desired shape using any suitable methods including, but not limited to, stamping, die cutting, laser cutting, or the like. The metal sheet 583 can be bent prior to cutting or can be bent after cutting or between cuts. Moreover, the bent metal sheet can have one bend or multiple bends. In some embodiments, a laser or other device can be used to etch the bent metal sheet 583 at edges or other sections of the piece to provide relief, to promote a tighter radii, or to reduce bowing on straight sections.

Preferably, the second portion 582 covers at least a portion of a major surface 570 of the electronics housing 514 and extends to an adjacent portion of the side surface 572 or the second major surface 574 or any combination thereof. In this manner, the perimeter 584 of the first major surface 570 is not solely formed of the first conductive material, but a portion of that perimeter 585 is formed of the second conductive material with higher resistance. In such an arrangement, a potential eddy current loop around, or near, the perimeter of the major surface 570 includes at least a portion of the higher resistance second conductive material. This will reduce or prevent the formation of eddy currents in view of the higher resistance of such a current loop, as compared to an electronics housing formed solely of the first conductive material. More preferably, a portion of the perimeter of each major surface 570, 574 (and, optionally, one or more of the side surface(s) 572) is formed of the higher resistance second conductive material, as illustrated in FIGS. 5A and 5B.

Figure 6:
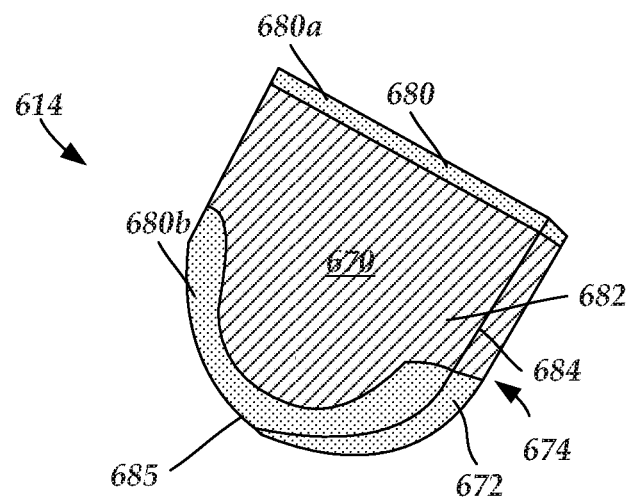
FIG. 6 is a schematic perspective view of a second embodiment of a composite electronics housing of a control module, according to the invention, according to the invention.

FIG. 6 illustrates another embodiment of an electronics housing 614 having a first major surface 670, a second major surface 674 opposite the first major surface, and at least one side surface 672 coupling the first and second major surfaces. The metal electronics housing 614 has at least two portions; at least one first portion 680 (in at least two parts, as illustrated in FIG. 6) that is formed of a first conductive material and at least one second portion 682 that is formed of a second conductive material. Preferably, the perimeter 684 of the first major surface 670 (and, optionally, one or more of the second major surface 674 and side surface(s) 672) is not solely formed of the first conductive material, but a portion of that perimeter 685 is formed of the second conductive material with higher resistance. The construction and design considerations of the elements in electronics housing 614 are the same as identically-named elements of electronics housing 514 unless indicated otherwise. In the embodiment of FIG. 6, the second portion 682 extends around a circumference of the electronics housing 514. It will be understood, however, that in other embodiments, the second portion does not extend around the entire circumference of the electronics housing. In the embodiment of FIG. 6, the second portion 682 separates the first portion 680 into two separate parts 680a, 680b. It will be understood, however, that in other embodiments, the second portion does not separate the first portion into separate parts.

Figure 7:
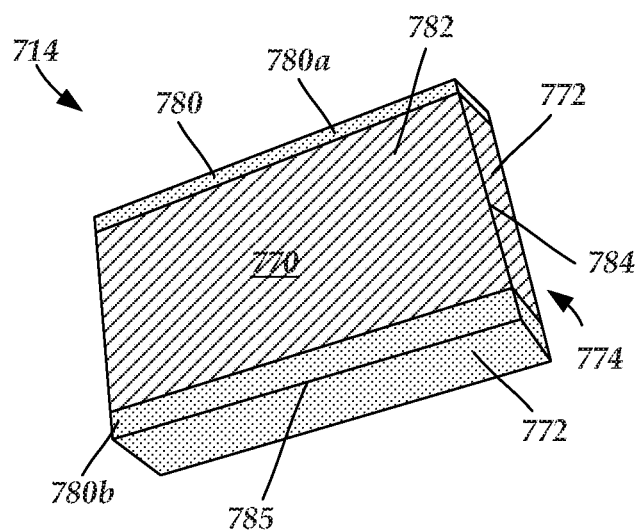
FIG. 7 is a schematic perspective view of a third embodiment of a composite electronics housing of a control module, according to the invention, according to the invention.

FIG. 7 illustrates another embodiment of an electronics housing 714 having a first major surface 770, a second major surface 774 opposite the first major surface, and at least one side surface 772 coupling the first and second major surfaces. The metal electronics housing 714 has at least two portions; a first portion 780 (in at least two parts, as illustrated in FIG. 7) that is formed of a first conductive material and a second portion 782 that is formed of a second conductive material. Preferably, the perimeter 784 of the first major surface 770 (and, optionally, one or more of the second major surface 774 and side surface 772) is not solely formed of the first conductive material, but a portion of that perimeter 785 is formed of the second conductive material with higher resistance. The construction and design considerations of the elements in electronics housing 714 are the same as identically-named elements of electronics housing 514 unless indicated otherwise. In the embodiment of FIG. 7, the second portion 782 extends around a circumference of the electronics housing 714. It will be understood, however, that in other embodiments, the second portion does not extend around the entire circumference of the electronics housing. In the embodiment of FIG. 7, the second portion 782 separates the first portion 780 into two separate parts 780a, 780b. It will be understood, however, that in other embodiments, the second portion does not separate the first portion into separate parts.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable control module for an electrical stimulation system, the control module comprising:
    a connector configured and arranged to couple to a lead or lead extension;
    an electronics housing coupled to the connector and having a first major surface, a second major surface opposite the first major surface, and at least one side surface coupling the first and second major surfaces, wherein the electronics housing comprises a first portion formed of a first conductive material and a second portion formed of a second conductive material, wherein the first conductive material has a resistivity that is no more than 50% of a resistivity of the second conductive material, wherein the second portion forms at least a region of the first major surface and extends to form an adjacent region of the at least one side surface or the second major surface; and
    an electronic subassembly disposed within the electronics housing and configured and arranged to electrically couple to the lead or lead extension through the connector.

2. The control module of claim 1, wherein the first conductive material has a resistivity that is no more than 33% of a resistivity of the second conductive material.

3. The control module of claim 1, wherein the first conductive material is titanium and the second conductive material is a titanium alloy.

4. The control module of claim 1, wherein the second portion extends to form the adjacent region of the at least one side surface and further extends to form an adjacent region of the second major surface.

5. The control module of claim 1, wherein the second portion is contiguous.

6. The control module of claim 1, wherein the second portion extends around an entire circumference of the control module.

7. The control module of claim 1, wherein the first portion is contiguous.

8. The control module of claim 1, wherein the first portion comprises a first part and a second part, wherein the second portion separates the first part from the second part.

9. An electrical stimulation system, comprising:
    the control module of claim 1; and
    a lead coupleable to the control module, the lead comprising a proximal end portion, a distal end portion, a plurality of electrodes disposed along the distal end portion, and a plurality of terminals disposed along the proximal end portion and electrically coupled to the plurality of electrodes.

10. The electrical stimulation system of claim 9, further comprising a lead extension coupleable to the lead and the control module.

11. The control module of claim 1, wherein the first major surface is a front of the electronics housing and the second major surface is a back of the electronics housing.

12. The control module of claim 1, wherein the first portion forms at least a second region of the first major surface and extends to form an adjacent second region of the at least one side surface or the second major surface.

13. The control module of claim 1, wherein the first portion forms at least a second region of the first major surface and extends to form an adjacent second region of the at least one side surface and further extends to form an adjacent second region of the second major surface.

14. The control module of claim 4, wherein the region of the first major surface formed by the second portion and the adjacent region of the second major surface formed by the second portion are disposed on opposite sides of the control module.

15. The control module of claim 4, wherein the region of the first major surface formed by the second portion and the adjacent region of the second major surface formed by the second portion have a same shape.

16. The control module of claim 4, wherein the adjacent region of the at least one side surface formed by the second portion is bent relative to the region of the first major surface formed by the second portion.

17. The control module of claim 16, wherein the adjacent region of the at least one side surface formed by the second portion is bent relative to the adjacent region of the second major surface formed by the second portion.

18. The control module of claim 1, wherein a first portion of a perimeter of the first major surface is formed of the first conductive material and a second portion of the perimeter of the first major surface is formed of the second conductive material.

19. The control module of claim 18, wherein a first portion of a perimeter of the second major surface is formed of the first conductive material and a second portion of the perimeter of the second major surface is formed of the second conductive material.

20. The control module of claim 1, wherein the first portion is not contiguous.

\* \* \* \* \*